(12) United States Patent
Morsi

(10) Patent No.: US 7,744,652 B2
(45) Date of Patent: Jun. 29, 2010

(54) ANEURYSM SEALING DEVICE

(76) Inventor: Hesham Morsi, 2045 Southgate Blvd., Houston, TX (US) 77030

( * ) Notice: Subject to any disclaimer, the term of this patent is extended or adjusted under 35 U.S.C. 154(b) by 749 days.

(21) Appl. No.: 11/562,475

(22) Filed: Nov. 22, 2006

(65) Prior Publication Data
US 2007/0173928 A1   Jul. 26, 2007

Related U.S. Application Data

(60) Provisional application No. 60/760,983, filed on Jan. 23, 2006.

(51) Int. Cl.
*A61F 2/02* (2006.01)
(52) U.S. Cl. .................. 623/23.72; 606/192; 606/193; 606/200
(58) Field of Classification Search .............. 623/23.72, 623/2.1, 2.11; 606/191–195, 200, 213; 128/836; 604/101.1, 101.3, 101.5
See application file for complete search history.

(56) References Cited

U.S. PATENT DOCUMENTS

| | | | | |
|---|---|---|---|---|
| 6,270,515 | B1 * | 8/2001 | Linden et al. | 606/213 |
| 6,855,154 | B2 * | 2/2005 | Abdel-Gawwad | 606/200 |
| 6,949,116 | B2 * | 9/2005 | Solymar et al. | 623/1.12 |
| 2001/0000797 | A1 * | 5/2001 | Mazzocchi | 606/151 |
| 2002/0026210 | A1 * | 2/2002 | Abdel-Gawwad | 606/194 |
| 2004/0034386 | A1 * | 2/2004 | Fulton et al. | 606/200 |
| 2004/0087998 | A1 * | 5/2004 | Lee et al. | 606/200 |
| 2004/0133222 | A1 | 7/2004 | Tran et al. | |
| 2004/0254625 | A1 * | 12/2004 | Stephens et al. | 623/1.1 |
| 2005/0131443 | A1 * | 6/2005 | Abdel-Gawwad | 606/191 |
| 2005/0288706 | A1 * | 12/2005 | Widomski et al. | 606/213 |
| 2006/0105014 | A1 * | 5/2006 | Cruise | 424/423 |

OTHER PUBLICATIONS

PCT International Search Report dated Oct. 1, 2007, for International Patent Application No. PCT/US07/60772.

* cited by examiner

*Primary Examiner*—(Jackie) Tan-Uyen T Ho
*Assistant Examiner*—Son Dang
(74) *Attorney, Agent, or Firm*—David McEwing

(57) ABSTRACT

A device useful for treating an aneurysm having a neck comprises a first inflatable disc and a second inflatable disc, said second inflatable disc being adjacent to said first inflatable disc and in fluid communication therewith. The inflatable discs are sized and constructed such that when the inflatable discs are inflated, the aneurysm neck is engaged therebetween. The inflatable discs may include at least one wall that is substantially inelastic and may include an internal member limiting expansion of the inflatable disc in a direction parallel to the device axis. The inflatable discs may have an aspect ratio greater than 3.

10 Claims, 5 Drawing Sheets

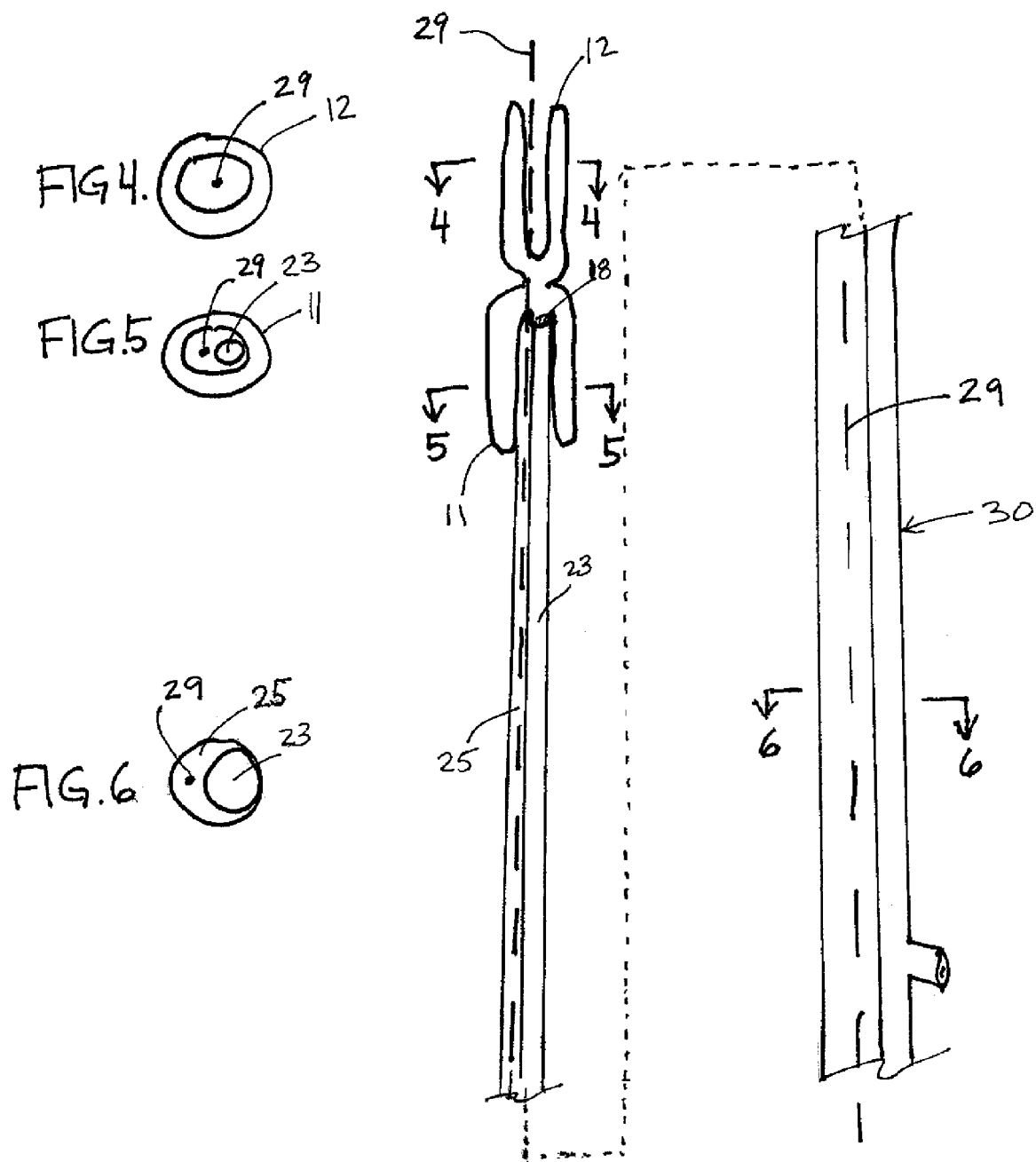

ANEURYSM SEALING DEVICE

CROSS-REFERENCE TO RELATED APPLICATIONS

This application claims priority to U.S. provisional application Ser. No. 60/760,983 filed Jan. 23, 2006, which is incorporated herein by reference.

STATEMENT REGARDING FEDERALLY SPONSORED RESEARCH OR DEVELOPMENT

Not Applicable.

FIELD OF THE INVENTION

The present invention relates generally to devices for treating a vascular aneurysm. More specifically, the present invention relates to a device having a pair of inflatable discs that engage the aneurysm opening between them so as to seal the aneurysm.

BACKGROUND OF THE INVENTION

A vascular aneurysm typically occurs when there is localized stretching or distension of an artery due to a weakening of the vessel wall. The vascular distension itself is often referred to as an aneurysm sac. The opening from the vessel to the aneurysm sack is often referred as the aneurysm neck. Often an aneurysm can be the site of internal bleeding and, if the aneurism ruptures, the site of a stroke.

Several methods for treating aneurysms have been attempted, with varying degrees of success. For example, surgical or extravascular approaches are common in the treatment of intra-cranial berry aneurysms; these are straightforward but fairly traumatic. The method involves removing a portion of the cranium and locating the aneurysm. The neck of the aneurysm is typically closed by applying a specially sized clip to the neck of the aneurysm. The surgeon may choose to perform a suture ligation of the neck or wrap the entire aneurysm. Each of these procedures is performed by a very intrusive invasion into the body and is performed from the outside of the aneurysm or target site. General anesthesia, craniotomy, brain retraction, and a placement of clip around the neck of the aneurysm all are traumatic. The surgical procedure is often delayed while waiting for the patient to stabilize medically. For this reason, many patients die from the underlying disease prior to the initiation of the surgical procedure.

Another procedure—the extra—intravascular approach—involves surgically exposing or stereotaxically reaching an aneurysm with a probe. The wall of the aneurysm is perforated from the outside and various techniques are used to occlude the interior of the aneurysm to prevent it from bleeding. The techniques used to occlude the aneurysm include electro-thrombosis, adhesive embolization, hoghair embolization, and ferromagnetic thrombosis Alternative treatments include endovascular occlusion, in which the aneurysm is entered with a guidewire or a microcatheter, which is then used to emplace an occluding means. The occluding means is typically an embolic device, such as one or more coils or other devices, or an amount of an in situ polymerizable compound. An occlusion is formed within the sac, which is intended to reduce blood flow into the aneurysm. Because items are being placed in the aneurysm sack, there is a risk that the sac will be overfilled; that some of emplaced devices may migrate into the parent vessel; and/or that the aneurysm sack may be damaged during the process. Aneurysms that have a wide opening between the aneurysm sac and the parent vessel are particularly difficult to treat.

Another disadvantage of detachable coils involves coil compaction over time. After filling the aneurysm, there remains space between the coils. Continued hemodynamic forces from the circulation act to compact the coil mass resulting in a cavity in the aneurysm neck. Thus the aneurysm can recanalize. In addition, aneurysms that have a wide opening between the aneurysm sac and the parent vessel are difficult to treat. This is particularly true of bifurcation aneurysms such as basilar tip aneurysms.

Another means for forming an occluding mass in an aneurysm sac involves the placement of an elastic inflatable disc in the aneurysm. Detachable occlusion inflatable discs are used in many types of medical procedures. These inflatable discs are typically carried at the end of a catheter and, once inflated, are detached from the catheter. Such an inflatable disc may be positioned within an aneurysm, filled and then detached from the catheter. Besides delivery complications, elastic inflatable discs may be subject to overfilling, which may rupture the aneurysm. Likewise, if the inflatable disc is under-filled, the result may be incomplete occlusion of the aneurysm.

Conventional detachable balloons also suffer disadvantages. For example, detachable balloons, when inflated, typically do not conform to the interior configuration of the aneurysm sac. Instead, the detachable balloon requires the aneurysm sac to conform to the exterior surface of the detachable balloon. Thus, there is an increased risk that the detachable balloon will rupture the sac of the aneurysm. Further, because they engage the aneurysm only poorly, detachable balloons can rupture and migrate out of the aneurysm.

Another means for treating vascular aneurysms involves the placement of a liner in the aneurysm sac. An aneurysm liner includes a liner sac that is placed in the aneurysm sac and filled so as to occlude the aneurysm. A guidewire is typically utilized to carry the liner through the vasculature and to assist in deploying the liner in the aneurysm. While the aneurysm liner concept is intuitively attractive, it has posed a number of technical challenges. One primary challenge involves the difficulty in producing a material that is robust enough to contain embolic material without inhibiting the ability of the embolic device to conform to the aneurysm geometry itself, rather than the geometry of the liner. In many instances, materials currently incorporated into aneurysm liner concepts are not compliant enough to adequately remodel the neck portion of an aneurysm sac. This disadvantage can lead to neck remnants and subsequently recanalization after embolization.

Most current aneurysm liners are physically inconvenient or inappropriate for treatment of large aneurysms. For example, many liner concepts involve forming the aneurysm liner of a woven or braided polymeric material such as polypropylene or polyester. These mesh materials are difficult to use in treating medium to large size aneurysms, for example, aneurysms 5-20 millimeters in diameter. Such mesh materials result in an assembly that is too bulky when collapsed down into the catheter for delivery. In other words, the amount of liner material required to fill a relatively large aneurysm is very difficult to collapse down into a constrained, low profile, delivery configuration small enough to be delivered and deployed without excess friction on the walls of the delivery catheter or other delivery lumen. The bulkiness of these devices makes them inconvenient or inappropriate for intra-cranial delivery.

Various other methods and devices are known in the art. However, currently none produces a satisfactory method for closing the aneurysm opening. Thus, it remains desirable to provide devices that can readily and consistently be placed in an aneurysm opening so as to close the opening without damaging the vessel or risking damage to the aneurysm sack.

SUMMARY OF THE INVENTION

The present invention is an aneurysm treatment device for treating aneurysms, including wide-and narrow-necked aneurysms, side-wall and bifurcation aneurysms, and aneurysms of different sizes.

In some embodiments, the invention comprises a device for treating an aneurysm in a blood vessel, the aneurysm having a neck and a sack, where the device includes a first inflatable disc and a second inflatable disc, the second inflatable disc being adjacent to the first inflatable disc and in fluid communication therewith, wherein the first and second inflatable discs are sized and constructed such that when one inflatable disc is positioned in the aneurysm sack and the discs are inflated, the aneurysm neck is engaged therebetween. Fluid flow between said first and second inflatable discs may be by means of a fluid passageway that includes a one-way valve. The device may include a guide wire on which said inflatable discs are mounted during placement. Each of said first and second inflatable discs preferably includes an inner wall and an outer wall. In preferred embodiments, at least one of said walls is substantially inelastic and at least one of said inner walls is elastic.

The invention also includes a method for treating an aneurysm in a blood vessel, the aneurysm having a neck and a sack, the method comprising: providing a device comprising a first inflatable disc and a second inflatable disc, said second inflatable disc being adjacent to the first inflatable disc and in fluid communication therewith; positioning the device at an aneurysm such that one inflatable disc is positioned in the aneurysm sack; and inflating the first and second inflatable discs such that the aneurysm neck is engaged therebetween.

BRIEF DESCRIPTION OF THE DRAWINGS

For a more detailed description of the preferred embodiment of the present invention, reference will now be made to the accompanying drawings, wherein:

FIG. 3 is a schematic side view of the device of FIG. 1 mounted on a catheter;

FIG. 4 is a cross-section taken along lines 4-4 of FIG. 3;

FIG. 5 is a cross-section taken along lines 5-5 of FIG. 3;

FIG. 6 is a cross-section taken along lines 6-6 of FIG. 3;

DETAILED DESCRIPTION OF THE PREFERRED EMBODIMENTS

Figure 1:
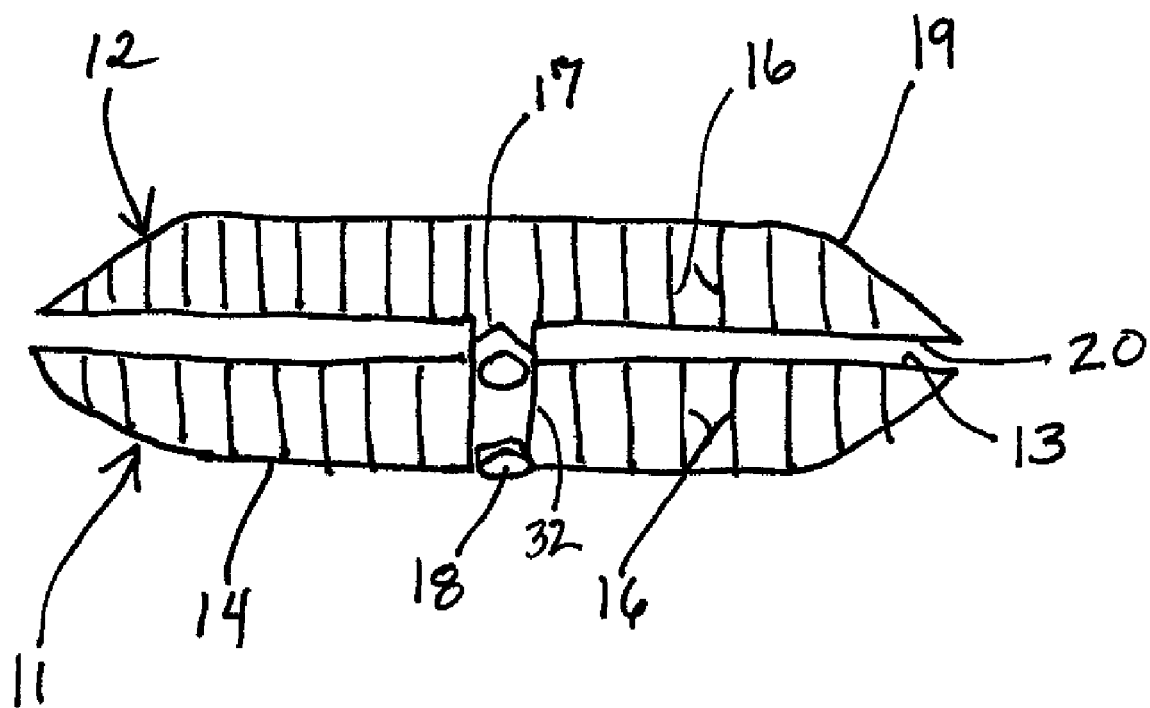
FIG. 1 is a schematic side view of a device constructed in accordance with one embodiment of the invention.
Figure 2:
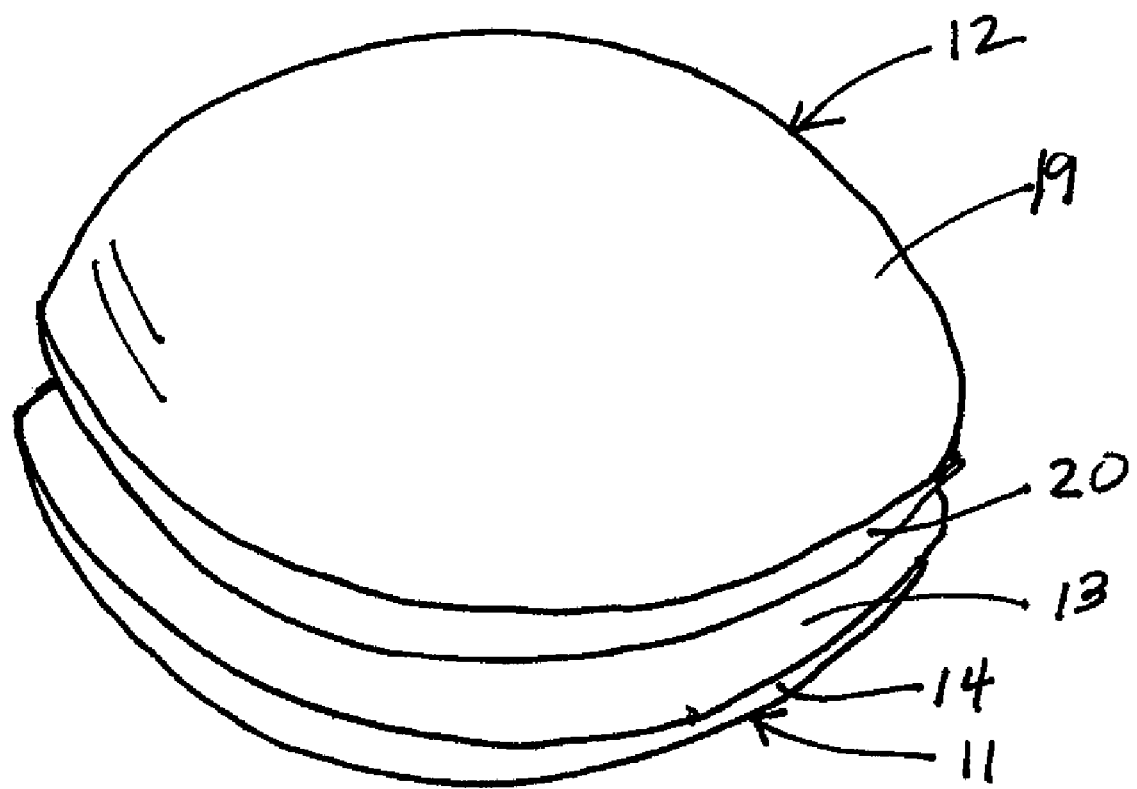
FIG. 2 is an oblique schematic top view of the device of FIG. 1 in an inflated state.

Referring initially to FIGS. 1 and 2, a device 10 constructed in accordance with a first embodiment of the invention includes a proximal inflatable disc 11 and a distal inflatable disc 12, which are connected by a channel 32. Proximal disc comprises an inner wall 13 and an outer wall 14. Inner and outer walls 13, 14 are each preferably made of an inelastic material and are preferably constructed of a biocompatible material such as polytetrafluoroethylene (PTFE).

Similarly, distal inflatable disc 12 comprises an inner wall 20 and an outer wall 19. Like outer wall 14, outer wall 19 is preferably constructed of an inelastic material, while inner wall 20 is preferably constructed of a semi-elastic or resilient material.

In preferred embodiments, the inner and outer walls of proximal and distal discs 13, 20 are preferably substantially curved so as to form an overall device that is concave when viewed from the distal end, for treatment of bifurcation aneurysms. In alternative embodiments, discs 13, 20 can be substantially planar for treatment of side-walls aneurysm. This configuration allows the device to conform to the vascular anatomy and the angle of the neck, which not only allows the closure of the aneurysm neck with minimal trauma, but also allow the outer surface of the device facing the parent artery to act as a flow modifier which decrease the hemodynamic effect of the flowing blood on the wall of the artery.

Thus, inner walls 13, 20 are preferably substantially planar, but can alternatively be more or less curved so as to form an overall device that is concave when viewed from the distal end. Outer walls 14, 19 are preferably each concave, or saucer-shaped, so that the perimeter of each inflatable disc is defined where outer walls 14, 19 meet inner walls 13, 20, respectively. The concave shape of outer walls 14, 19, can be formed using partial spherical surfaces, frustoconical surfaces, parabolic surfaces, and variations thereof. The perimeter of each inflatable disc 11, 12, is sealed by fusing the two inner walls 13, 20 together so as to form a seal therebetween. It will be understood that, in some instances, the inner and outer walls may be formed of a single piece of material, in which case the terms "inner" and "outer" are indicative of the relative positions of the walls.

In many instances, it is desirable to minimize the disruption of blood flow through the main vessel that is caused by the aneurysm sealing device. Thus, in some embodiments, the perimeter and/or edges of the present device are constructed so as to provide gently curved interfaces with the adjacent vessel wall so that blood flow past the device is substantially laminar. By providing a smooth profile on the flow side of the device, blood flow past the device is enhanced. In addition the edges of the present devices may be constructed and/or treated so as to encourage intimal growth of the surrounding tissue, which would enhance retention of the device in the desired location.

In alternative embodiments (not shown), outer walls 14, 19 are substantially planar and are sealed to inner walls 13, 20 at the outer edge of each inflatable disc by a circumferential member extending between each pair of walls. It will be understood that the precise configuration and method of constructing the present device is not limited to those methods and configurations described herein.

Between each pair of inner and outer walls, within the volume of each inflatable disc, at least one web 16 connects the inner surfaces of the walls. In certain embodiments a plurality of webs 16 is included within each disc. Webs 16 are preferably constructed of a substantially inelastic material and are preferably extend in a generally longitudinal direction, so that they prevent each inflatable disc from expanding more than a predetermined amount in the longitudinal direction. Similarly, the substantially planar and inelastic nature of inner walls 13, 20, prevents the inflatable discs from excessive expansion in the radial direction. Thus, the construction of each inflatable disc ensures that it will expand to substantially the shape illustrated in the figures, or a predetermined variation thereof, and to a predetermined volume. For example, in many embodiments, the maximum longitudinal length of each disc (along the tool axis) may be 1 mm or less, e.g. less than 25% of the diameter of the parent artery and the sac of the aneurysm. Similarly, the maximum horizontal diameter is preferably at least 2 mm larger than the diameter of the neck so that it can completely span the neck of the aneurysm and extend for at least 1 mm beyond the neck, so as to engage the surrounding tissue.

In certain embodiments, each inflatable disc is substantially disk-or saucer-shaped when in its inflated state. More specifically, each inflatable disc has a substantially circular perimeter and an aspect ratio greater than 3. In preferred embodiments, each inflatable disc may have an aspect ratio greater than 4 or greater than 5. In other embodiments, the perimeters of each inflatable disc may be other than circular, such as elliptical or oval. In other embodiments, one or both inflatable discs may be selected from a range of inflatable disc sizes and/or shapes, or may be custom-made to fit a particular aneurysm or other vascular malformation.

Proximal disc 11 is preferably in fluid communication with a first lumen 23 of a delivery catheter 30 via a detachable valve 18, break away connection or a simple quick connection. An exemplary valve is a self-closing membrane similar to those found in needle injection ports of intravenous fluid bags. Fluid can be injected into disc 11 via lumen 23, thereby inflating disc 11.

According to one embodiment, proximal disk 11 is preferably also attached to and in fluid communication with distal disc 12 through a pressure controlled one-way valve 17, which opens when the pressure difference between proximal disc 11 and distal disc 12 exceeds a predetermined level, whereupon fluid is allowed to flow from proximal disc 11 into distal disc 12. In this manner, distal disc 12 can be inflated without deflating proximal disc 11. Because valve 17 allows fluid flow only when the pressure differential between the discs exceeds a predetermined value, flow into distal disc will correspond to increases in pressure in proximal disc 11. Therefore, if the injection of fluid into disc 11 is incremental, fluid flow into distal disc 12 will likewise be incremental.

It will be understood that various other means could be used to inflate the discs. For example each disc could be provided with its own fluid delivery lumen. In this embodiment, inflation and deflation of each disc would be independent of the level of inflation of the other disc.

Referring now to FIGS. 3-6, the delivery catheter is preferably provided with a second lumen 25, which may be adjacent to or concentric with first lumen 23. Second lumen 25 provides a passageway for a guide wire, as described below. Second lumen 25 preferably terminates adjacent to the proximal side of proximal disc, where it aligns with an artificial lumen 26 that is formed, prior to deployment of the device, by folding or rolling deflated discs 11, 12 so as to define an axial passageway for the guidewire. Deflated discs 11, 12 can each be folded or rolled in either a proximal or distal direction, as desired.

Figure 7:
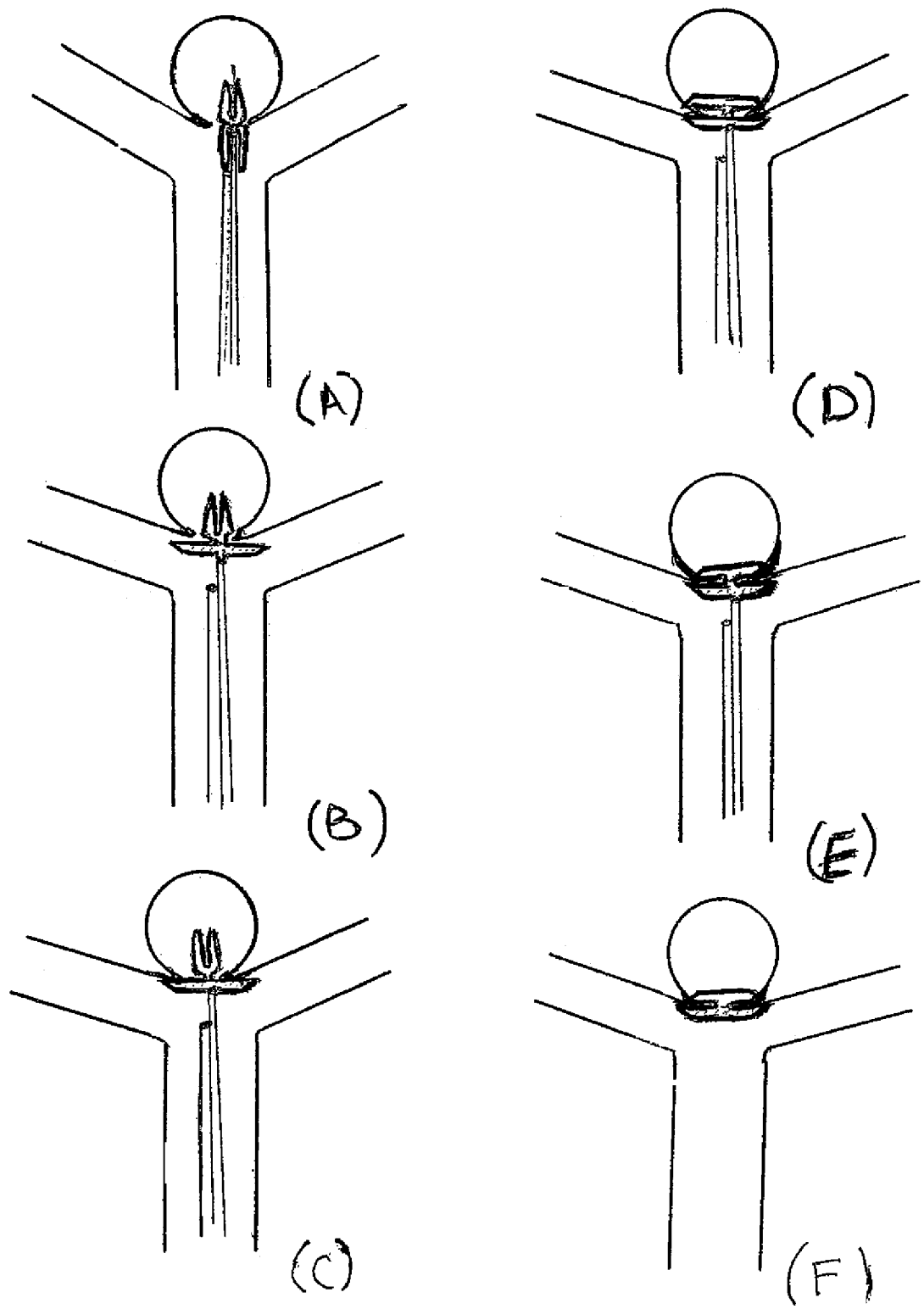
FIGS. 7(A)-(F) are sequential schematic views of the device of FIG. 1 being deployed at an aneurysm opening.

When it is desired to treat an aneurysm using the present device 10, a positioning microwire 29 (shown in phantom) is inserted through second lumen 25 so that it extends distally beyond distal inflatable disc 12. Both inflatable discs are in their collapsed states. The positioning wire 29 is threaded to the site of the aneurysm and fluoroscopic imaging is used to position the wire 29 such that its tip is at or in the aneurysm and the distal disc is within the aneurysm, as shown in FIG. 7(A). At this point, fluid, which may be a polymerizable compound, is pumped through lumen 23 and flows into proximal disc 11, causing it to inflate and assume its expanded state, as shown in FIG. 7(B). Before proximal disc 11 is fully inflated, device 10 is preferably advanced along wire 29 until proximal disc 11 is placed against the neck of the aneurysm, as shown in FIG. 7(C). At the point, the aneurysm is at least partially sealed. If desired, sealing of the neck can be verified by injecting contrast proximal the device while keeping proximal disk 11 against the neck of the aneurysm. If no contrast enters the aneurysm, it is sealed.

Additional fluid can then be pumped into device 10, where it enters proximal disc 11. When proximal disc 11 is full, valve 17 opens, allowing fluid to enter distal disc 12. As additional fluid is added, distal disc 12 expands within the aneurism until it has assumed its final shape, as shown in FIG. 7(D). Once distal disc 12 is full, the addition of a small amount of fluid will cause the semi-elastic inner wall 20 to stretch or deform slightly toward proximal disc 11, thereby firmly engaging the neck of the aneurysm around the perimeter of device 10 as shown in FIG. 7(E). The engagement of the aneurysm neck between the inflatable discs of the device seals the neck and reinforces the adjacent weak vessel wall.

The injected material is preferably a fluid, such as a flowable polymeric material that, when injected into the channels, solidifies in situ by, for example, a change in pH or ionic concentration of the polymer, exposure to organic solvents, introduction of a secondary material capable of precipitation, or exposure of the material in the one or more channels to heat or light, for example, a laser. The occluder may be hardened through a cooperative effect of coagulation, precipitation, or ionization of the patient's blood in the region of the occluder. Likewise, the fluid may be a polymer, or may include a polymer, monomer, cross-linkers, and/or initiators. The polymerization system can be converted to a semi-solid, e.g., a hydrogel, or to a solid after its introduction into the channel. Examples of polymers and polymerization systems useful in the practice of the invention include, but are not limited to, polyphosphazenes, polyethylene glycols, polybutadienes, polyacrylates, polydiacrylates, polyurethanes, polyacrylamides, polyvinylpyrrolidone, collagen, carbohydrates such as chitosan, polylysines, polylactic acids, and combinations Once the desired amount of fluid has been placed in the device, the catheter is disconnected from the device as shown in FIG. 7(F). The polymer, if used, hardens with the device, rendering it rigid and permanent.

In an alternative embodiment, outer walls 14, 19 and inner wall 20 are constructed of an inelastic material, but inner wall 13 is constructed of a semi-elastic or resilient material. Valve 17 is again provided, but in this embodiment allows fluid to flow from distal inflatable disc 12 into proximal inflatable disc 11. Similarly, lumen 23 is in fluid communication with distal inflatable disc 12, rather than proximal inflatable disc 11.

Figure 8:
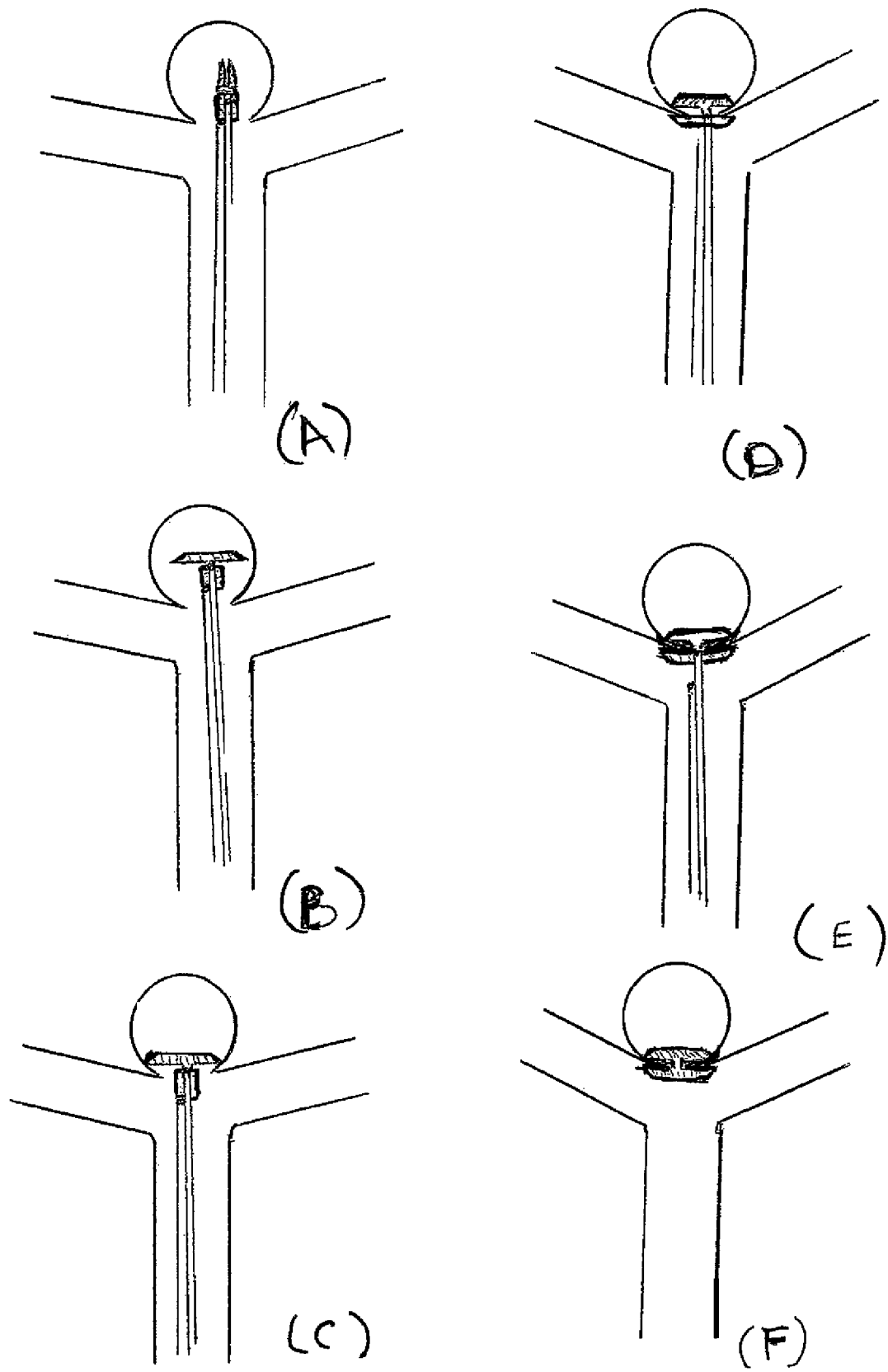
FIGS. 8(A)-(F) are sequential schematic views of an alternative embodiment of the device being deployed at an aneurysm opening.

When it is desired to treat an aneurysm using this embodiment of the present device, the device is again guided into position using microwire 29. The positioning wire 29 is threaded to the site of the aneurysm and fluoroscopic imaging is used to position the wire 29 such that its tip is at or in the aneurysm and the distal disc is within the aneurysm, as shown in FIG. 8(A). At this point, a fluid, which may be a polymerizable compound, is pumped through lumen 23 and flows into distal disc 12, causing it to inflate and assume its expanded state, as shown in FIG. 8(B). Before distal disc 12 is fully inflated, device 10 is preferably retracted slightly along wire 29 until distal disc 12 is set against the neck of the aneurysm, as shown in FIG. 8(C). At the point, the aneurysm is at least partially sealed. If desired, sealing of the neck can be verified by injecting contrast proximal the device while keeping distal disc 12 against the neck of the aneurysm. If no contrast enters the aneurysm, it is sealed.

Additional fluid can then be pumped into device 10, where it enters distal disc 12. When distal disc 12 is full, valve 17 opens, allowing fluid to enter proximal disk 11. As additional fluid is added, proximal disk 11 expands against the neck of the aneurysm until it has assumed its final shape, as shown in FIG. 8(D). Once proximal disk 11 is full, the addition of a small amount of fluid will cause the semi-elastic inner wall 13 to stretch or deform slightly toward distal disc 12, engaging the neck of the aneurysm around the perimeter of device 10 as above as shown in FIG. 8(E). The engagement of the aneurysm neck between the inflatable discs of the device seals the neck and reinforces the adjacent weak vessel wall. The device can be disconnected from the catheter and allowed to harden, if desired, as shown in FIG. 8(F).

Several mechanisms help ensure that the present device can be deployed without damaging the surrounding vessel. The inelastic disc walls and inelastic webs prevent each disc from expanding beyond its desired ultimate shape. Similarly, use of a digital inflating device to inject the fluid allows the continuous monitoring of the pressure inside the inflating disc. In addition, the use of a radio-opaque inflating fluid allows visual monitoring of the shape of the device. Each of these allows close control of the disc size and placement.

Once deployed, the present devices remain and provide permanent closure of the aneurysm. Because the neck of the aneurism is engaged between the two inflatable discs, the device is fixed in position. Likewise, because the device fully occludes the aneurysm neck, there is no fluid flow into the aneurysm and it ceases to grow.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. A device for treating an aneurysm in a blood vessel, the aneurysm having a neck and a sack, comprising:
    a first inflatable disc; and
    a second inflatable disc, said second inflatable disc being adjacent to said first inflatable disc and in fluid communication therewith;
    a pressure controlled one-way valve controlling a fluid communication pathway between the first and second discs and comprising the opening of said valve when the pressure difference between the discs exceeds a predetermined level and the valve pressure control prevents over inflation of the discs;
    wherein said first and second inflatable discs comprise a plurality of webs made from substantially inelastic material extending from one interior side of the disc to the opposing side of the disc so that the webs prevent each inflatable disc from expanding more than a predetermined amount; and
    wherein said first and second inflatable discs are sized and constructed such that when one inflatable disc is positioned in the aneurysm sack and said first and second inflatable discs are inflated, the aneurysm neck is engaged there between.

2. The device in accordance with claim 1, further including a guide wire on which said inflatable discs are mounted during placement.

3. The device in accordance with claim 1 wherein each of said first and second inflatable discs includes an inner wall and an outer wall and at least one of said walls is substantially inelastic.

4. The device in accordance with claim 1 wherein each of said first and second inflatable discs includes an inner wall and an outer wall, wherein at least one of said walls is substantially inelastic, and wherein at least one of said inner walls is elastic.

5. The device in accordance with claim 1 wherein at least one of said first and second inflatable discs has an aspect ratio greater than 3 of width to height.

6. The device in accordance with claim 1 wherein said first and second inflatable discs are each concave when viewed from the distal end.

7. The device of claim 1 wherein said first inflatable disc and said second inflatable disc are elliptical.

8. The device of claim 1 wherein at least one of first inflatable disc or second inflatable disc has a curved profile so as to maintain laminar blood flow.

9. The device of claim 1 wherein at least one of first inflatable disc has a flat profile so as to maintain laminar blood flow.

10. The device of claim 3 wherein the outer wall of each inflatable disc comprises a partial spherical surface, a frusto-conical surface, or a parabolic surface to minimize disruption of blood flow through the blood vessel.

* * * * *